United States Patent [19]

Suzuki

[11] Patent Number: 4,997,939
[45] Date of Patent: Mar. 5, 1991

[54] PROCESS FOR PREPARING ADENINE

[75] Inventor: Jiro Suzuki, Yatsushiro, Japan

[73] Assignee: Kohjin Co., Ltd., Tokyo, Japan

[21] Appl. No.: 323,709

[22] Filed: Mar. 15, 1989

Related U.S. Application Data

[60] Division of Ser. No. 571,150, Jan. 17, 1984, Pat. No. 4,861,883, which is a continuation of Ser. No. 285,805, Jul. 22, 1981, abandoned.

[30] Foreign Application Priority Data

| Mar. 21, 1980 | [JP] | Japan | 55-34723 |
| Mar. 21, 1980 | [JP] | Japan | 55-34724 |
| Aug. 5, 1980 | [JP] | Japan | 55-108046 |
| Oct. 13, 1980 | [JP] | Japan | 55-141960 |

[51] Int. Cl.$^5$ .................................. C07D 473/34
[52] U.S. Cl. .................. 544/277; 534/582; 534/739
[58] Field of Search ................ 544/277; 534/582, 739

[56] References Cited

U.S. PATENT DOCUMENTS

| 2,658,889 | 11/1953 | Goldberg et al. | 534/739 |
| 3,213,124 | 10/1965 | Sheppard | 534/739 X |
| 3,382,228 | 5/1968 | Ferrari et al. | 534/739 X |
| 4,092,314 | 5/1978 | van der Zwan | 544/277 |

FOREIGN PATENT DOCUMENTS

| 0780858 | 3/1968 | Canada | 544/277 |
| 1416000 | 11/1964 | France | |
| 0001780 | 8/1968 | Japan | |
| 0081394 | 8/1974 | Japan | |
| 0023516 | 7/1976 | Japan | |
| 1207475 | 10/1970 | United Kingdom | 544/277 |

OTHER PUBLICATIONS

Kirk–Othmer, Encyclopedia of Chemical Technology, 2nd, ed., vol. 4, p. 156 (1964).

Primary Examiner—Diana G. Rivers
Attorney, Agent, or Firm—Armstrong, Nikaido, Marmelstein, Kubovcik & Murray

[57] ABSTRACT

A process for preparing adenine by reacting an arylazomalononitrile with formic acid or its derivatives in the presence of ammonia and then subjecting the intermediate pyrimidine derivative to a reaction under catalytic reduction condition. Adenine can be prepared in high purity and high yields without isolating the intermediate pyrimidine derivative, when ammonia is removed before conducting the reaction under catalytic reduction condition. Also, the preparation of adenine in high purity and high yields can be more surely attained, when the arylazomalononitrile prepared under a specific condition is employed as a starting material or when Raney nickel is employed as a reduction catalyst in combination with active carbon. The produced adenine is effectively purified by separation of insoluble materials from an aqueous hot solution of adenine adjusted to pH 7.5 to 9.0 and formation of a mineral acid salt of adenine followed by decoloration by heating in the presence of active carbon.

6 Claims, 1 Drawing Sheet

PROCESS FOR PREPARING ADENINE

This is a division of application Ser. No. 571,150 filed Jan. 17, 1984, now U.S. Pat. No. 4,861,883, which is a continuation of application Ser. No. 285,805, filed Jul. 22, 1981, now abandoned.

BACKGROUND OF THE INVENTION

The present invention relates to a process for preparing adenine, and more particularly to a process for preparing adenine by thermally reacting an arylazomalononitrile of the general formula (I):

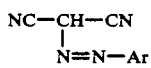
(I)

wherein Ar is an aryl group, with formic acid or its derivatives in the presence of ammonia, and subjecting the resulting pyrimidine derivative to catalytic reduction substantially in the absence of ammonia.

Hitherto, there are known processes for the preparation of adenine using the arylazomalononitrile [I] as a starting material, e.g. in examined Japanese Patent Publication (Tokkyo Kokoku) No. 23516/1976, Unexamined Japanese Patent Publication (Tokkyo Kokai) No. 81394/1974 and U.S. Pat. No. 4,092,314.

Japanese Patent Publication No. 23516/1976 discloses a process for preparing adenine in a single process step, in which adenine is prepared by reacting an arylazomalononitrile with a formic acid derivative in the presence of ammonia under a catalytic reduction condition. Japanese Patent Publication No. 81394/1974 and U.S. Pat. No. 4,092,314 disclose a process for preparing adenine in two process steps, in which an arylazomalononitrile is first thermally reacted with a formic acid derivative in the presence of ammonia to produce a pyrimidine derivative of the general formula (II):

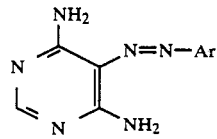
(II)

wherein Ar is an aryl group, and after isolating the pyrimidine derivative (11) or without conducting the isolation, the pyrimidine derivative (II) is subsequently reacted with a formic acid derivative under a catalytic reduction condition. In the reaction of the second step under catalytic reduction condition, hydrogenation of the pyrimidine derivative (II) and ring closure reaction of the resulting triaminopyrimidine take place.

These processes are superior to previously known processes for the preparation of adenine, but are not always satisfactory in the yield and purity of the obtained crude adenine. That is to say, the former process of one stage is simple in procedure, but the yield and purity are insufficient. In the latter process of two stages, adenine of a good purity is obtained in a good yield when the pyrimidine derivative (II) is once isolated and the reaction under catalytic reduction condition is then carried out, but the isolation procedure is very troublesome and is hard to apply to industrial preparation. When the reaction of the second step is successively carried out without taking out the pyrimidine derivative (II) from the reaction system, the yield and purity of the obtained adenine are not sufficient, and also it is hard to obtain adenine in a constant yield. In these known processes, amorphous greenish gray materials are by-produced as impurities, thus resulting in lowering of the yield and purity of the product.

The thus produced crude adenine has been generally purified in a manner in which a mixture of the crude adenine and water, e.g. water 40 to 50 times the amount of adenine, is refluxed to dissolve adenine and then decolored with an adsorbent such as active carbon. As special instances of purification, there are also known a process in which adenine is adsorbed by passing through a column of active carbon and is eluted with aqueous ammonia., a process using a cation-exchange resin (e.g. commercially available under the commercial name "Amberlite IR-120B" made by Rohm & Haas Co.); and a process in which impurities are oxidatively decomposed with potassium permanganate under an acidic condition to remove them and decoloration is then conducted with active carbon. Purification by sublimation is also proposed.

However, these purification processes are not satisfactory processes. In case of the above-mentioned general purification process by refluxing of a mixture of crude adenine and water followed by decoloration with active carbon, the purity and whiteness are insufficient, and the other purification processes also have problems in purity, purification loss and cost.

SUMMARY OF THE INVENTION

It is a primary object of the present invention to provide a process for preparing adenine in high yields and high purity.

A further object of the invention is to prepare adenine directly from the arylazomalononitrile (I) in high yields and high purity without isolating the intermediate pyrimidine derivative (II) by a two stage process in which the arylazomalononitrile is thermally reacted with formic acid or its derivatives in the presence of ammonia and the resulting pyrimidine derivative is then reacted with formic acid or its derivative under a catalytic reduction condition A still further object of the invention is to provide a starting material, an arylazomalononitrile, having a good quality suitable for preparing adenine of high purity in high yields.

A further object of the invention is to provide a process for preparing adenine of high purity in high yields in a shortened period of reaction time.

Another object of the invention is to provide a process for purification to give adenine of high purity and high whiteness.

These and other objects of the present invention will become apparent from the description hereinafter.

It has now been found that in the preparation of adenine by the reaction of an arylazomalononitrile with formic acid or its derivatives in the presence of ammonia with heating, followed by the reaction under catalytic reduction condition of the intermediate 4,6-diamino-5-arylazopyrimidine, ammonia present at the time of the catalytic reduction causes the lowering of the yield and purity of adenine, and accordingly the yield and purity can be increased without isolating the intermediate 4,6-diamino-5-arylazopyrimidine when the catalytic reduction is carried out after removal of ammonia.

DETAILED DESCRIPTION

Figure 1:
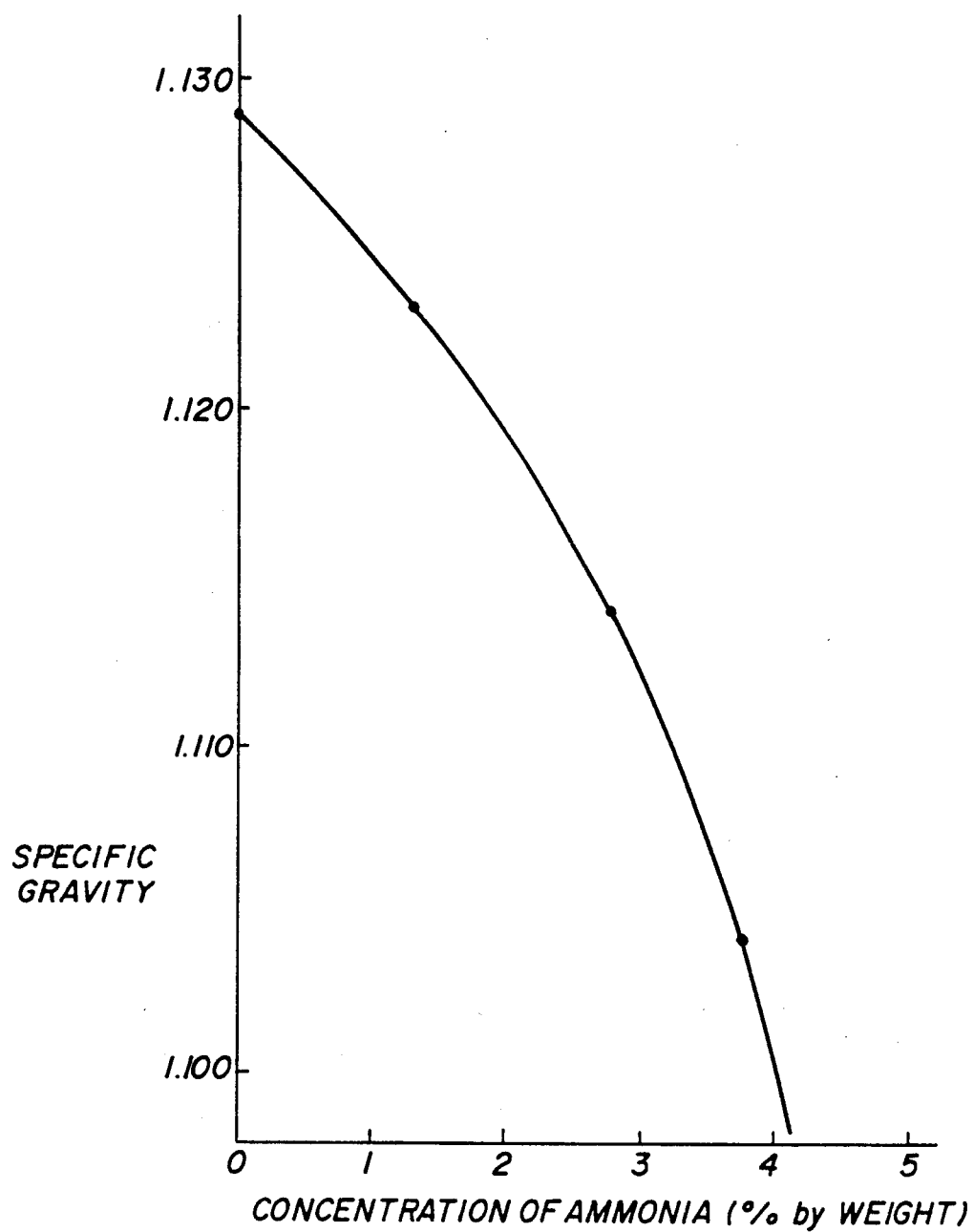
FIG. 1 is a graph showing the relationship between the specific gravity of formamide containing ammonia and the concentration of ammonia, which is used as a calibration curve for determining the concentration of ammonia remaining after removal procedure of ammonia according to the present invention.

In the present invention, an arylazomalonitrile of the general formula (1):

wherein Ar is an aryl group, is reacted with formic acid or its derivatives in the presence of ammonia at an elevated temperature, and after removing the ammonia from the reaction system so that ammonia is not substantially present in the reaction system, in other words, ammonia is not present in the reaction system in such an amount as exerting an influence on the yield and purity of adenine, the resulting pyrimidine derivative of the general formula

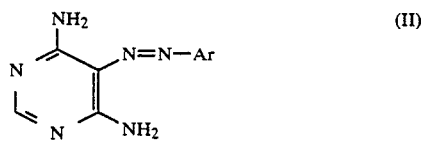

wherein Ar is as defined above, is subjected to a reaction under a catalytic reduction condition to produce adenine. The aryl group of the arylazomalononitrile (I) may be any of aromatic groups, but in case of aromatic groups having a substituent, it is desirable to avoid the use of those having a high reactive substituent in preventing a side reaction.

In carrying out the catalytic reduction, it is the most preferable that ammonia is absolutely absent in the reaction system, in other words, the amount of ammonia present in the reaction system is 0% by weight. In practice, however, it is possible to sufficiently attain the objects of the present invention, if the amount of ammonia present in the reaction system is not more than 2% by weight, at most 5% by weight, based on the liquid component of the reaction system.

The intermediate pyrimidine derivative (II) is gradually converted into an amorphous material under the catalytic reduction condition by ammonia, and accordingly ammonia exerts a bad influence on the catalytic reduction so as to not only directly lower the yield in the catalytic reduction and the purity of the product, but also hinder the catalytic reduction.

In order to prevent the conversion of the pyrimidine derivative (II) by ammonia so as to decrease the bad influence of ammonia, it is desirable to increase the reaction rate of catalytic reduction and to make the reaction temperature as low as possible. For instance, the bad influence of ammonia may be prevented to some extent in such a manner that while increasing the reaction rate by raising the hydrogen pressure and making as uniform as possible with sufficient agitation the reaction system containing the pyrimidine derivative (II) which is slightly soluble in a solvent such as formamide, the catalytic reduction is conducted at a temperature of 120° to 140° C., though the preferable temperature in the second step is from 120° to 160° C. However, this manner depends on the performance of a reactor, and has a limit. Therefore, it is difficult to prepare adenine of high purity in high yields by only such a reaction manner, and the removal of ammonia is still necessary.

A manner of removing ammonia is not particularly limited, and any manners are adoptable if efficiently practicable before conducting the catalytic reduction. For instance, ammonia may be removed in a manner in which since the reaction in the first step for forming the pyrimidine derivative (II) is carried out in a closed reactor usually at an elevated temperature of 120° to 160° C., the residual pressure is released while still hot after the completion of the reaction in the first step; a manner in which the reaction mixture is cooled once and the pressure is reduced; a manner in which a gas such as nitrogen gas is bubbled through the reaction mixture; or a combined manner thereof. In case of industrially practicing the process of the invention, a combination of a manner of releasing ammonia in still hot and a manner of bubbling a gas such as nitrogen gas is preferable, since the former is simple in procedure and the latter gas bubbling also serves as nitrogen replacement of a reactor which is conducted for catalytic reduction in the next step.

The reaction in the first step for producing the intermediate pyrimidine derivative (II) is usually carried out at a temperature of 120° to 160° C. for 1 to 10 hours. The reaction is conducted in a closed vessel, since it is conducted in the presence of ammonia. The pyrimidine derivative (II) is produced in a conversion of 90 to 97%.

The aryl group of the arylazomalononitrile (I) may be any aromatic groups. Also, the aromatic groups may contain a substitutent group, but a high reactive substituent group is undesirable for preventing side reaction.

Examples of the derivative of formic acid used in the present invention are formamide, N,N-dimethylformamide, esters of formic acid such as ethyl formate, orthoformic acid esters such as methyl orthoformate and ethyl orthoformate, formamidine salts such as formamidine acetate, and the like. Formamide is preferred, because of being inexpensive and easy to obtain and handle.

Although the use of a solvent is not particularly required when formamide or ethyl formate is employed in the reaction, solvents may be employed as diluents, e.g. lower alcohols having 1 to 4 carbon atoms, ethers such as tetrahydrofuran and dioxane, and ethylene glycol ethers such as cellosolve and butyl cellosolve. In case of employing formamidine salts in the reaction, the lower alcohols and ethers are preferably employed as solvents.

Although the theoretical amount of formic acid or its derivatives is an equimolar amount to an arylazomalononitrile, in practice formic acid or its derivatives are employed in an amount 2 to 50 times the molar amount of the arylazomalononitrile. The reason is that the produced pyrimidine derivative (II) is slightly soluble in formic acid or its derivative and, therefore, the excess as a diluent is required, though a smaller amount is sufficient when the above-mentioned diluent is employed.

Ammonia is employed in an amount of 1.5 to 10 moles per mole of an arylazomalononitrile, though an equimolar amount is the theoretical amount. When the amount of ammonia is more than the above range, the pyrimidine derivative (II) is of course produced, but its yield and purity are lowered.

After the completion of the first step reaction, ammonia remaining in the reaction system is removed. For instance, when the reaction is conducted at a temperature of 150° to 155° C. for 2 to 5 hours by employing 10 parts by weight of formamide and 6 moles of ammonia based on an arylazomalononitrile, the residual pressure in a closed reactor is about 8 to 9 kg./cm.$^2$G. In one of preferred embodiments, ammonia is removed by releasing the residual pressure in the reactor while the reaction mixture is still hot (hereinafter referred to as "hot release method"). A valve of the reactor is gradually opened to release a volatile gas. In that case, attention should be paid since sudden opening of the valve causes blowoff of the content. Although it is of course desirable that the removal of ammonia is conducted at high temperatures, the removal operation at a reaction temperature is convenient. Most of the ammonia can be removed by such a method, and the amount of ammonia in the reaction system can be decreased to less than 2% by weight based on the liquid component of the reaction system, though it varies depending on the composition of the reaction system and the operation temperature. In order to further raise the removal efficiency, introduction of an inert gas such as nitrogen gas into the reaction system, gradual reduction of pressure in the system or bubbling of an inert gas under reduced pressure may also be adoptable.

In another embodiment of the removal, after the completion of the reaction, a reactor is cooled to 30° to 50° C. from the outside, and after removing the inner pressure by opening a valve of the reaction, an inert gas such as nitrogen gas is bubbled through the reaction mixture or the pressure of the reaction system is reduced (hereinafter referred to as "pressure reduction method"). In case of simply adopting the bubbling procedure, for instance, when nitrogen gas is introduced at a rate of 500 ml./min. at 28° C. for 1 hour through a glass tube of 8 mm. in inner diameter into 300 g. of formamide containing 8.89% by weight of ammonia, the residual ammonia is 3.20% by weight. Therefore, the bubbling procedure is rather suitable as an auxiliary means for the hot release method or the pressure reduction method Subsequently, the reaction under a catalytic reduction condition in the second step is carried out without isolating the pyrimidine derivative (II) produced in the first step. In this second reaction, the pyrimidine derivative (II) is catalytically reduced into 4,5,6-triainopyrimidine which then reacts with formic acid or its derivative to produce adenine. The catalytic reduction catalysts used in the invention may be any of the known hydrogenation catalysts. The term "catalytic reduction condition" as used herein means the condition of catalytic reduction using, for instance, a combination of hydrogen and reduced nickel catalyst, a combination of hydrogen and Raney nickel catalyst, a combination of hydrogen and palladium catalyst, or the like. The second reaction is carried out at a temperature of 120° to 180° C. for 1 to 10 hours, especially 3 to 7 hours.

The process of the present invention in which the first and second steps are succesively carried out without isolating the intermediate product is very advantageous as an industrial process for the preparation of adenine, and according to the process of the present invention, adenine of high purity can be prepared in high yields.

The raw material, arylazomalononitriles (I) can be easily prepared by azo coupling of diazonium salts of aromatic amines with malononitrile. Aniline is general as an aromatic amine, but other various substituted aromatic primary amines may be usable. The properties such as color and odor, namely the purity, of the obtained arylazomalononitrile varies depending on the condition of the preparation.

The present inventor has made a study on the relationship between the condition for preparing the arylazomalononitrile and the yield and purity of adenine prepared therefrom, and has found that arylazomalononitriles prepared under a specific condition has a high purity and when it is employed as a raw material for preparing adenine, adenine can be very advantageously prepared. That is to say, arylazomalononitriles prepared by conducting the coupling reaction of diazonium salts and malononitrile at a temperature no: more than 25° C. at pH 3.5 to 5.5 and drying the product to not more than 5% by weight in water content are usable as they are without purification and are very suitable as a raw material, and produce good results in purity and yield of adenine.

An aqueous solution of a diazonium salt which is usually acidic and malononitrile are admixed. Upon neutralizing the mixture with an alkaline compound, the coupling reaction temperature is maintained at 25° C. or below, preferably 10° to 20° C. and the mixture is adjusted to pH 3.5 to 5.5, preferably pH 4 to 5, and the aging is then conducted at a temperature of 10° to 20° C. for 3 to 30 hours, preferably 3 to 10 hours. The produced brilliant yellow crystal is filtered and dried at a temperature not more than 70° C., preferably not more than 65° C. until the water content becomes at most 5% by weight, preferably at most 2% by weight.

The diazonium salt is prepared by the reaction of a salt of an aromatic amine such as aniline or a substituted aniline and sodium nitrite according to a usual process for the preparation of a diazonium salt. The reaction is carried out at a temperature of not more than 12° C., preferably 5° to 10° C. The total reaction time including the time of adding dropwise sodium nitrite to the reaction system is from 2 to 15 hours, preferably 2 to 10 hours. When the diazonium salt prepared under conditions outside the above ranges is employed for the preparation of the arylazomalononitrile, not only the yield of the arylazomalononitrile is lowered, but also it exerts an influence on the yield of adenine. The theoretical amount of sodium nitrite is one mole per mole of an aromatic primary amine, and it is known in a literature that sodium nitrite is usually employed in an amount of 1.2 to 1.3 moles per mole of the amine. However, the excess of sodium nitrite not only changes the color of the coupling reaction product to brown, but also causes a singular odor of $NO_x$ to remain in the produced arylazomalononitrile and to change the color to brown during drying. Accordingly, it is desirable to employ sodium nitrite in an as small amount as possible, e.g. 1.05 to 1.1 mole per mole of the aromatic primary amine. Moreover, in order to remove the residual nitrous acid component, it is desirable to add a compound able to react with nitrous acid at low temperatures, such as ammonium sulfamate or urea.

In a preferred embodiment, the arylazomalononitrile (I) is prepared in the following manner. A diazonium salt of an aromatic amine is prepared by adding the aromatic primary amine to a to 5 to 25%, preferably 10 to 20%, by weight mineral acid solution, cooling the solution to not more than 10° C., adding dropwise an aqueous solution of sodium nitrite to the cooled solution to conduct the diazotation at a temperature of 5° to 10° C., after the dropwise addition further aging for 1 to 2 hours, and adding an aqueous solution of ammonium sulfamate to the reaction mixture until the color of an iodo-starch paper is unchanged. The thus prepared solution of a diazonium salt is a transparent light yellow solution and is employed in the next diazo-coupling reaction. Malononitrile in the form of an aqueous solution or dispersion is admixed with the diazonium solution, and the mixture is neutralized with an alkaline compound with cooling. Although the alkaline compound is not particularly limited, there are usually employed sodium hydroxide, potassium hydroxide, sodium carbonate and sodium acetate and from the viewpoint of heat generation and easiness in pH adjustment, sodium acetate is particularly preferred. It is necessary to maintain the temperature at 25° C. or below, preferably 10° to 20° C. during the neutralizaiton, and at that temperature, the mixture is adjusted to pH 3.5 to 5.5, preferably pH 4 to 5. After the neutralization, the reaction for aging is further carried out at that temperature for 3 to 30 hours, preferably 3 to 10 hours. The produced brilliant yellow crystal is filtered and washed with water until the filtrate becomes neutral. The washed crystal is then dried at a temperature of not more than 70° C., preferably not more than 65° C. until the water content becomes not more than 5% by weight, preferably not more than 2% by weight. When the water content is more than 5% by weight, the yield and purity of adenine are lowered, since an arylazomalononitrile, a reacting reagent such as formic acid or its derivatives, and the pyrimidine derivative are hydrolyzed.

When the thus prepared arylazomalononitrile is employed as a starting material for preparing adenine, the by-production of amorphous greenish gray materials can be decreased and thus the objects of the present invention can be more surely attained.

Further, the present inventor has studied on the prevention of production of by-products from another aspect, and has also found that when Raney nickel is employed as a hydrogenation catalyst in combination with active carbon, the time of the catalytic reduction to produce triaminopyrimidine can be shortened and adenine can be prepared in high yields and high purity. It has not been known to carry out the reduction using Raney nickel in the presence of active carbon.

According to the present inventor's study, the yield and purity of adenine has a correlation with the time required in catalytic reduction, and the reason is considered to be that the intermediate pyrimidine derivative (II) undergoes a change to convert into an amorphous material by ammonia and the amorphous material covers the active points of the catalyst so as to inactivate the catalyst, thus hindering the reduction raction. The present inventor has found that this problem can be solved by utilizing active carbon.

The use of Raney nickel combined with active carbon is very useful, since the inactivation of the catalyst is prevented by active carbon and consequently the reduction time can be shortened and moreover the yield and purity of adenine can be further increased. When Raney nickel combined with active carbon is employed in catalytic reduction of the intermediate pyrimidine derivative (II), the objects of the present invention can be more surely and advantageously attained.

The amount of active carbon is selected from 1 to 300% by weight, preferably 50 to 200% by weight, based on Raney nickel.

In a preferred embodiment, the reaction of the arylazomalononitrile (I) is carried out in a pressure vessel in excess of formic acid or a derivative thereof such as formamide in the presence of ammonia at a temperature of 120° to 160° C. for several hours, and after removing ammonia from and adding Raney nickel and active carbon to the reaction system, the produced intermediate pyrimidine derivative (II) is reacted, without the isolation, in formic acid or its derivative in the presence of Raney nickel and active carbon at a temperature of 120° to 180° C., for several hours under hydrogen pressure. The active carbon may be added at the time of starting the first reaction for producing the pyrimidine derivative (II), though it is preferably added at the time of the second reaction with Raney nickel.

The second reaction condition and procedure may be the same as those in the case using no active carbon, and no change is required by the use of active carbon. It is convenient to add to the reaction system Raney nickel and active carbon in the form of a suspension in a reaction solvent, but the manner of addition is not limited thereto.

Adenine prepared according to the process of the present invention has an improved purity as compared with that prepared by a conventional process, but still contain a trace amount of impurities. In order to obtain adenine having a high purity and a high whiteness, the crude adenine is purified. The purification may be carried out in a conventional manner, e.g. reflux of water containing crude adenine to separate insoluble materials followed by decoloration with active carbon. However, according to a conventional purification manner, the purified adenine is still lacking in whiteness, though the purity is high.

The present inventor has also found that by-products can be precipitated as water-insoluble materials from a hot aqueous solution of crude adenine by adjusting the solution to a weak basic solution of pH 7.5 to 9.0 and if desired, further adding a salt such as Glauber's salt or sodium chloride, and that decoloration can be effectively conducted by adding a mineral acid such as sulfuric acid, hydrochloric acid or phosphoric acid to the system to lower the pH to a point at which adenine forms a salt with the mineral acid, or below, and then heating together with active carbon. Adenine having a very high purity and a high whiteness can be obtained by combining these two processes.

After the completion of the reduction of the pyrimidine derivative (II) and the cyclization into adenine, the reaction solvent is recovered from the reaction mixture, and to the residue is added water in an amount of 35 to 80 times, preferably 45 to 60 times the volume of the residue. The mixture is then adjusted to pH 7.5 to 9.0, preferably pH 7.5 to 8.5 with an alkaline compound, preferably sodium hydroxide, and as occasion demands, thereto was further added an inorganic salt in an amount of 10 to 100% by weight, preferably 2.5 to 50% by weight, based on the residue. The mixture is then heated to dissolve adenine, and insoluble materials such as impurities and catalyst are removed by filtration while it is still hot. A mineral acid is then added to the filtrate to lower the pH of the filtrate to a pH capable of forming a salt, i.e. below about pH 3, preferably pH 2.5 to 1.5, and after adding active carbon, the decoloration is conducted with heating. The waste active carbon is then removed by filtration, and the filtrate is neutralized with an alkaline compound such as sodium hydroxide and cooled to precipitate a crystalline adenine. The thus purified adenine has a high purity and a high whiteness. In the above purification, adenine may be taken out as a crystal in every step. Also, in the step of removing by-products, the pH adjustment is of couse combined with the addition of an inorganic salts.

The alkaline compound used in the purification includes sodium hydroxide, sodium potassium, sodium carbonate, potassium carbonate, calcium hydroxide, or the like, and in general sodium hydroxide is conveniently employed. The inorganic salt includes Glauber's salt, sodium chloride, ammonium carbonate, ammonium hydrogenphosphate, or the like, and Glauber's salt is conveniently employed.

As a process of the removal of amorphous by-products, the present inventor made a study on oxidation with hydrogen peroxide, sodium hypochlorite or potassium permanganate, and reduction with acetic acid-zinc or sodium dithionite, but these processes are low in effect as compared with the purification process of the present invention. The present inventor also make a study on decoloration by means of an ion-exchange resin, but the effect is insufficient. The purification of crude adenine according to the present invention is very useful, and when the present process for the preparation of adenine is combined with this purification process, adenine having a high purity and a high whiteness can be very advantageously obtained in high yields.

The present invention is more specifically described and explained by means of the following Examples.

The yield as shown herein is calculated as follows:

$$\text{Yield (\%)} = \frac{\text{Amount of adenine obtained (g.)}}{\text{Theoretical amount of adenine produced (g.)}}$$

The purity of the product, the content of impurity and the amount of ammonia as shown herein are determined as follows:

(1) Purity

The purity is determined by comparing the absorbance at a wavelength of 262 nm. of a $5 \times 10^{-4}$ % by weight solution in 0.1N-HCl with that of the standard solution.

(2) Impurity

The content of impurities is determined by calculation according to area normalization method from a chromatogram obtained by a high performance liquid chromatography through a column of a cation-exchange resin.

(3) Amount of ammonia

There is no suitable method for directly determining the amount of ammonia remaining in the reaction system, and accordingly it is determined on the basis of the following model experiment.

Formamide is cooled from the outside with ice-cold water, and ammonia gas is bubbled through formamide to saturate ammonia. The formamide saturated with ammonia is employed as a starting sample. The sample is heated in a closed vessel at a prescribed temperature for 1 hour with agitation, and is then subjected to the following ammonia removal procedure. The specific gravity is measured by areometer, and the residual ammonia concentration (% by weight) is determined from the previously prepared calibration curve shown in FIG. 1.

(1) Hot release method

A valve of the closed vessel is gradually opened under ordinary pressure, while agitating the hot sample.

The results of the ammonia removal by the hot release method are shown in Table 1.

(2) Pressure reduction method

The hot sample is cooled to 30° C., and at that temperature, the pressure of the closed vessle is reduced to a prescribed pressure with agitating the sample.

The results of the ammonia removal by the pressure reduction method are shown in Table 2.

TABLE 1

| | Initial | 30° C. | 87° C. | 110° C. | 150° C. |
|---|---|---|---|---|---|
| Concentration of ammonia (%) | 8.89 | 3.44 | 1.35 | 1.24 | trace |

TABLE 2

| | Initial | 90 mmHg | 50 mmHg | 20 mmHg |
|---|---|---|---|---|
| Concentration of ammonia (%) | 8.89 | 1.35 | 1.24 | trace |

REFERENCE EXAMPLE

An influence of ammonia on catalytic reduction of the intermediate pyrimidine deriVative (11) was observed.

To 111 g. of formamide containing a prescribed amount of ammonia as shown in Table 3 was added 14.0 g. of 4.6-diamino-5-phenylazopyrimidine, and after adding 1.3 g. of Raney nickel to the mixture, the catalytic reduction was carried out in an autoclave at a temperature of 130° to 135° C. for 1 hour under an initial hydrogen pressure of 50 kg./cm.$^2$. The temperature was then raised, and the reaction was further continued at a temperature of 150° to 155° C. for 4 hours.

The reaction mixture was cooled, and excess formamide was recovered under reduced pressure. To the residue were added 280 ml. of water, 2 g. of Glauber's salt and 0.7 g. of active carbon, and the mixture was refluxed for 1 hour and filtered in still hot to remove insoluble materials. The filtrate is then cooled to precipitate adenine, and the crystal is filtered and dried.

The amount and yield of the adenine obtained are shown in Table 3.

TABLE 3

| | Ammonia | | Adenine | |
|---|---|---|---|---|
| Run No. | Amount (g.) | Concentration (% by weight) | Amount (g.) | Yield (%) |
| 1 | 0 | 0 | 7.51 | 85.0 |
| 2 | 1.13 | 1 | 7.29 | 82.5 |
| 3 | 2.29 | 2 | 7.25 | 82.1 |
| 4 | 3.46 | 3 | 7.11 | 80.5 |
| 5 | 4.67 | 4 | 6.81 | 77.1 |
| 6 | 5.89 | 5 | 6.33 | 71.7 |
| 7 | 9.74 | 8 | 4.78 | 54.1 |

From Table 3, it is seen that when the amount of ammonia at the time of the catalytic reduction of the intermediate pyrimidine derivative (II) is at most 5% by weight, preferably at most 2% by weight, adenine can be prepared in high yields.

EXAMPLE 1

In 680 g. of formamide containing 6% by weight of ammonia was dissolved 68.1 g. of phenylazomalononitrile, and the reaction was carried out in an autoclave at a temperature of 150° to 155° C. for 2 hours with agitation. After the reaction, the agitation speed was decreased and immediately ammonia was released by gradually opening the valve of the autoclave. After the residual pressure in the autoclave became 0 kg./cm.$^2$G, heating was stopped and the reaction mixture was allowed to cool. The residual ammonia was trace, i.e. less than 1% by weight.

After the cooling, 10 g. of Raney nickel was added to the autoclave, and the catalytic reduction was carried out at a temperature of 130° to 135° C. for 1 hour under an initial hydrogen pressure of 50 kg./cm.$^2$. At that stage, absorption of hydrogen was 90% of theoretical. The temperature was then raised, and the reaction was further continued at a temperature of 150° to 155° C. for 4 hours. After cooling, the reaction mixture was taken out from the autoclave, and formamide was recovered by reduced pressure distillation. To the residue was added 2.5 liters of water, and after dissolving most of the residue by refluxing, insoluble materials were removed from the hot solution by filtration. Active carbon was then added to the filtrate and was heated for 1 hour to decolor. The active carbon was then filtered and the filtrate was cooled to precipitate adenine. The crystal was filtered and dried. The obtained adenine was 41.2 g. and the yield was 76.2%. The purity of the obtained adenine was 98.5% by weight, and the content of impurity was 0.76% by weight.

COMPARATIVE EXAMPLE 1

The procedure of Example 1 was repeated except that the ammonia removal procedure was not conducted.

The obtained adenine was 33.5 g. and the yield was 62.0%. The purity of the obtained adenine was 95.0% by weight and the content of impurity was 4.76% by weight.

EXAMPLE 2

The procedure of Example 1 was repeated except that after the completion of the reaction in the first step, ammonia was released by cooling the reaction mixture and gradually reducing the pressure to 30 mmHg. The amount of ammonia remaining in the system before starting the catalytic reduction was about 1% by weight.

The obtained adenine was 41.5 g. and the yield was 76.8%. The purity of the adenine was 98% by weight and the content of impurity was 1.10% by weight

EXAMPLE 3

In 680 g. of formamide containing 3% by weight of ammonia was dissolved 68.1 g. of phenylazomalononitrile, and the reaction was carried out in an autoclave at a temperature of 140° to 145° C. for 5 hours with agitation. After the completion of the reaction, the agitation speed was decreased, and immediately ammonia was released by gradually opening the valve of the autoclave and then bubbling nitrogen gas through the reaction mixture. The amount of ammonia was trace. After cooling the reaction mixture to room temperature, 5.0 g. of 5% by weight Pd/C was added to the autoclave, and the catalytic reduction was carried out at a temperature of 150° to 155° C. under an initial hydrogen pressure of 20 kg./cm.$^2$. After about 75 minutes, absorption of hydrogen was 85% of theoretical. At that temperature, the reaction was further continued for 4 hours. After cooling, the reaction mixture was taken out from the autoclave, and formamide was recovered by reduced pressure distillation. To the residue was added 2.5 liters of water, and the mixture was refluxed. After removing insoluble materials by filtration in still hot, active carbon was added to the filtrate and decoloration was carried out by heating it for 1 hour. The active carbon was filtered off and the filtrate was cooled to precipitate adenine. The crystal was filtered and dried to give 43.7%. of adenine. The yield was 80.8%. The purity of the obtained adenine was 98.5% by weight and the content of impurity was 0.77%.

EXAMPLE 4

In 50 g. of methanol containing 10% by weight of ammonia was dissolved 8.5 g. of phenylazomalononitrile, and thereto was added 74.1 g. of ethyl orthoformate. The reaction was carried out in an autoclave at a temperature of 150° to 155° C. for 5 hours with agitation. After cooling the reaction mixture to 120° C. by air-cooling, ammonia was released. The amount of the residual ammonia was about 1% by weight. The reaction mixture was then cooled, and after adding 1.5 g. of Raney nickel., the catalytic reduction was carried out at a temperature of 140° to 145° C. for 5 hours under an initial hydrogen pressure of 80 kg./cm.$^2$. After cooling, the reaction mixture was taken out from the autoclave.

The reaction mixture was concentrated under reduced pressure, and to the residue was added 300 ml of water and was refluxed to dissolve most of the residue. The still hot solution was filtered to remove insoluble materials, and after adding active carbon to the filtrate, decoloration was carried out by heating for 1 hour. The active carbon was filtered off, and the filtrate was cooled to precipitate adenine. The crystal was filtered and dried to give 4.7 g. of adenine. The yield was 69.6%. The purity of the obtained adenine as 98.3% by weight, and the content of impurity was 1.11% by weight.

EXAMPLE 5

In 100 g. of ethyl cellosolve containing 5% by weight of ammonia was dissolved 8.5 g. of phenylazomalononitrile, and thereto was added 31.2 g. of formamidine acetate. The reaction was carried out in an autoclave at a temperature of 130° to 135° C. for 5 hours. The reaction mixture was cooled, and nitrogen gas was bubbled through the reaction mixture to remove ammonia, while reducing the inner pressure. Then, 1.0 g. of 5% by weight pd/C was added to the reaction mixture, and the catalytic reduction was carried out at a temperature of 130° to 135° C. for 5 hours under an initial hydrogen pressure of 40 kg./cm.$^2$.

After cooling and taking out the reaction mixture from the autoclave, the reaction mixture was treated in the same manner as in Example 4 to give 5.1 g. of adenine. The yield was 75.6%. The purity of the obtained adenine was 98.9% by weight, and the content of impurity was 0.63% by weight.

EXAMPLE 6

In 680 g. of formamide containing 6% by weight of ammonia was dissolved 68.1 g. of phenylazomalononitrile, and thereto was added 10 g. of 5% by weight Pd/C. The reaction was conducted in an autoclave at 150° to 155° C. for 2 hours with agitation. After the reaction the agitation speed was decreased, and immediately ammonia was released by gradually opening the valve of the autoclave. Nitrogen gas was then introduced into the autoclave to 2 kg./cm.$^2$G. and was released. This procedure was repeated 3 times. The amount of the residual ammonia was almost 0% by weight. Hydrogen gas was then introduced into the autoclave, and the catalytic reduction was carried out at a temperature of 130° to 135° C. for 1 hour under an initial hydrogen pressure of 50 kg./cm.$^2$. The temperature was raised, and the reaction was further continued at a temperature of 155° to 160° C. for 5 hours.

The reaction mixture was treated in the same manner as in Example 1 to give 42.0 g. of adenine. The yield was 77.7%. The purity of the obtained adenine was 99.3% by weight, and the content of impurity was 0.52% by weight.

COMPARATIVE EXAMPLE 2

The procedure of Example 6 was repeated except that 6.8 g. of ammonium chloride was added to the reaction system and the ammonia removal procedure was not conducted.

The amount of the obtained adenine was 34.8 g. and the yield was 64.2%. The purity of adenine was 96.1% by weight, and the content of impurity was 8.8% by weight.

The above results show that the process of the present invention in which adenine is prepared by conducting catalytic reduction in the substantial absence of ammonia, is an excellent process capable of providing adenine of a high purity in high yields.

COMPARATIVE EXAMPLE 3

In 180 g. of formamide containing 12% by weight of ammonia was dissolved 17.0 g. of phenylazomalononitrile, and thereto were added 2.1 g. of ammonium chloride and 2 g. of 5% by weight Pd/C. The reaction was carried out in an autoclave at 150° C. for 5 hours with agitation. Hydrogen gas was then introduced into the autoclave, and the catalytic reduction was carried out at 150° C. for 5 hours under an initial hydrogen pressure of 80 kg./cm.$^2$.

After cooling, the reaction mixture was taken out, and formamide was recovered by reduced pressure distillation. To the residue was added 50 ml. of 2N NaOH to dissolve adenine, and the catalyst was separated by filtration. The filtrate was neutralized to precipitate adenine. The precipitate was filtered and dried to give 8.6 g. of adenine. The yield was 63.7%. The purity of the obtained adenine was 95.3% by weight, and the content of impurity was 2.5% by weight.

On the other hand, the above procedure was repeated except that before introducing hydrogen gas to the autoclave, ammonia gas was released by gradually opening the valve of the autoclave to decrease the residual amount to less than 1% by weight. The amount of the obtained adenine was 10.0 g., and the yield was 74.0%. The purity was 98.8% by weight, and the content of impurity was 0.77% by weight. From this result, the effect of the removal of ammonia is clear.

EXAMPLE 7

In 680 g. of formamide containing 6% by weight of ammonia was dissolved 68.1 g. of phenylazomalononitrile, and the reaction was carried out in an autoclave at a temperature of 150° to 155° C. for 2 hours. Ammonia gas was then released, so the amount of the residual ammonia was about 2% by weight.

After cooling the reaction mixture to room temperature, 10 g. of Raney nickel and 5 g. of active carbon were added to the reaction mixture, and the catalytic reduction was carried out at a temperature of 130° to 135° C. for 45 minutes under an initial hydrogen pressure of 50 kg./cm$^2$. The absorption of hydrogen was 95% of theoretical. The temperature was then raised, and the reaction was further continued at a temperature of 150° to 155° C. for 4 hours The reaction mixture was cooled and taken out from the autoclaved, and formamide was recovered by reduced pressure distillation. To the residue was added 2.5 liters of water, and was refluxed. After removing insoluble materials by filtration and adding 10 g. of active carbon to the filtrate, decoloration was conducted by heating for 1 hour. The active carbon was filtered off and the filtrate was cooled to precipitate adenine. The precipitate was filtered with suction and dried to give 43.9 g. of adenine. The yield was 81.2%. The purity of the obtained adenine was 98.7% by weight, and the content of impurity was 0.95% by weight.

EXAMPLES 8 TO 11

The procedures of Example 7 were repeated except that the amount of the active carbon used in the catalytic reduction was changed.

The results are shown in Table 4.

TABLE 4

| Ex. No. | Active carbon (g.) | Adenine | | | |
| --- | --- | --- | --- | --- | --- |
| | | A-mount (g.) | Yield (%) | Purity (% by weight) | Impurity (% by weight) |
| 8 | 0 | 37.9 | 70.1 | 97.5 | 1.94 |
| 9 | 1 | 41.8 | 77.3 | 98.5 | 1.03 |
| 10 | 10 | 44.3 | 82.0 | 99.2 | 0.85 |
| 11 | 20 | 43.5 | 80.5 | 99.0 | 0.27 |

EXAMPLES 12

The procedure of Example 7 was repeated except that the active carbon was present in the system from the start of the reaction for producing the intermediate pyrimidine derivative.

The amount of the obtained adenine was 42.8 g. and the yield was 79.2%. The purity of the adenine was 98.3% by weight and the content of impurity was 0.88% by weight.

EXAMPLE 13

An autoclave was charged with 21.5 g. of p-nitrophenylazomalononitrile and 143 g. of formamide containing 6% by weight of ammonia. The reaction was carried out at a temperature of 150° to 155° C. for 5 hours with agitation. After the completion of the reaction, ammonia was immediately released while the reaction mixture was still hot. After cooling the reaction mixture and adding 4 g. of Raney nickel and 3 g. of active carbon to the reaction mixture, the catalytic reduction was carried out at a temperature of 150° to 155° C. for 5 hours under an initial hydrogen pressure of 62 kg./cm$^2$ with shaking. The reaction mixture was cooled and taken out, and was then treated in the same manner as in Example 7 to give 11.8 g. of adenine. The yield was 87.4%. The purity of the obtained adenine was 98.6% by weight, and the content of impurity was 1.1 % by weight.

The results of Examples 7 to 13 show that the use of Raney nickel in combination with active carbon is effective in shortening the reaction time and raising the yield.

EXAMPLE 14

(i) Preparation of arylazomalononitrile

To 1914.7 g. of a 10% by weight hydrochloric acid was added 195.6 g. of aniline, and the mixture was cooled from the outside to 5° C. with ice-cold water. An aqueous solution of 152.2 g. of sodium nitrite dissolved in 304.4 ml. of water was gradually added dropwise to the solution of aniline hydrochloride over 2 hours, while maintaining the temperature at 6° to 7° C. At that temperature, the reaction was further continued for 2 hours. After the completion of the reaction, a 10% by weight aqueous solution of ammonium sulfamate was added until an iodo-starch paper was not colored to give an aqueous solution of a diazonium salt.

In 5 ml. of water was dissolved 118.9 g. of malononitrile with heating, and after cooling the solution, the above solution of diazonium salt was added thereto. The mixture was gradually neutralized with a 35% by weight aqueous solution of sodium acetate, while maintaining the reaction temperature at 15° to 20° C. by cooling with ice-cold water. From about pH 1, brilliant yellow crystal began to precipitate, and with the progress of the neutralization, the reaction system became pasty such that the agitation was difficult. The neutralization was stopped at pH 4.5, and thereafter aging was conducted at a temperature of 10° to 15° C. for 5 hours. The precipitated brilliant yellow crystal was filtered and washed with water until the filtrate became neutral. The crystal was dried in a hot air drier at 65° C. for 20 hours to give 293.1 g. of phenylazomolono-nitrile. The properties of the product were as follows:

Melting point: 137° to 138° C. (partial decomposition)
U.V. $\lambda_{Max}^{EtOH}$nm. ($\epsilon$): 244 (8,200), 359 (20,000)
Weight loss on drying: 0.56% by weight (2 g., 65° C., vacuum)

(ii) Preparation of adenine

In 680 g. of formamide containing 6% by weight of ammonia was dissolved 68.1 g. of the phenylazomalononitrile obtained in the above item (i), and the reaction was carried out in an autoclave at a temperature of 150° to 155° C. for 2 hours. Ammonia was released immediately after the completion of the reaction, so the amount of the residual ammonia was about 2% by weight.

After cooling the reaction mixture to room temperature, 10 g. of Raney nickel and 5 g. of active carbon were added to the reaction mixture, and the catalytic reduction was carried out at a temperature of 130° to 135° C. for 45 minutes under an initial hydrogen pressure of 50 kg./cm.$^2$. The absorption of hydrogen was 95% of theoretical. The temperature was then raised, and the reaction was further continued at a temperature of 150° to 155° C. for 4 hours.

The reaction mixture was cooled and taken out from the autoclave, and formamide was recovered by reduced pressure distillation. To the residue was added 2.5 liters of water, and was refluxed. After filtering off insoluble material, 10 g. of active carbon was added to the filtrate and decoloration was conducted by heating for 1 hour. The active carbon was filtered off and the filtrate was cooled to precipitate adenine. The precipitate was filtered with suction and dried to give 43.9 g. of adenine. The yield was 81.2%. The purity of the obtained adenine was 98.7% by weight, and the content of impurity was 0.95% by weight.

EXAMPLE 15

The procedure of Example 14(i) was repeated except that a 10% by weight aqueous solution of sodium hydroxide was employed instead of a 35% by weight aqueous solution of sodium acetate, to give 291.0 g. of yellow phenylazomalononitrile. The melting point was 135° to 138° C. (partial decomposition) and the weight loss on dying (2 g, 65° C., vacuum) was 0.88% by weight.

By employing the thus obtained phenylazomalononitrile, adenine was prepared in the same manner as in Example 14(ii).

The results are shown in Table 5.

EXAMPLES 16

The procedure of Example 14(i) was repeated except that the drying was conducted for 6 hours, to give 298.2 g. of phenylazomalononitrile. The melting point was 133° to 137° C. (partial decomposition), and the weight loss on drying (2 g., 65° C., vacuum) was 2.5% by weight.

By employing the thus obtained phenylazomalononitrile, adenine was prepared in the same manner as in Example 14(ii).

The results are shown in Table 5.

EXAMPLES 17 TO 20

In Example 17, the procedure of Example 14(i) was repeated except that the dropwise addition of the aqueous solution of sodium nitrite was conducted at a temperature of 12° to 15°C. for 6 hours to give 263.4 g. of yellowish brown phenylazomalononitrile. The melting point of the obtained phenylazomalononitrile was 130° to 135° C. (decomposition , and the weight loss on drying (2 g., 65° C., vacuum) was 0.93% by weight In Example 18, the procedure of Example 14(i) was repeated except that the neutralization of the mixture of malononitrile and the diazonium salt solution was conducted with sodium hydroxide at a temperature of 30° to 35° C. to give 278.7 g. of yellowish brown phenylazomalononitrile. The melting point of the obtained phenylazomalononitrile was 131° to 135° C. (decomposition), and the weight loss on drying (2 g., 65° C., vacuum) was 0.82% by weight.

In Example 19, the procedure of Example 14(i) was repeated except that the neutralization of the mixture of malononitrile and the diazonium salt solution was conducted with sodium hydroxide to pH 6.5 to give 266.5 g. of orangish yellow phenylazomalononitrile. The melting point of the obtained phenylazomalononitrile was 130° to 135° C. (decomposition), and the weight loss on drying (2 g., 65° C., vacuum) was 0.98% by weight.

In Example 20, the procedure of Example 14(i) was repeated except that the drying time was 4 hours, to give 332.0 g. of phenylazomalononitrile. The melting point of the obtained phenylazomalononitrile was 128° to 135° C. (partial decomposition), and the weight loss on drying (2 g., 65° C. , vacuum was 9.5% by weight.

By employing the phenylazomalononitrile so obtained in each Example, adenine was prepared in the same manner as in Example 14(ii).

TABLE 5

| Ex. No. | Adenine Amount (g.) | Yield (%) | Impurity (% by weight) |
|---|---|---|---|
| 15 | 43.4 | 80.3 | 0.99 |
| 16 | 40.8 | 75.5 | 1.08 |
| 17 | 31.9 | 59.0 | 1.68 |
| 18 | 29.2 | 54.0 | 1.53 |
| 19 | 33.0 | 61.1 | 1.24 |
| 20 | 28.6 | 52.9 | 1.91 |

The results of Examples 14 to 16 show that an arylazomalononitrile prepared under a particular condition are very suitable as a raw material for preparing adenine, and can provide adenine of high purity in high yields. On the other hand, it would be understood that phenylazomalononitrile obtained in Examples 17 to 19 contain impurities which would exert a bad influence on the preparation of adenine and it is necessary to purify it before using it as a raw material for preparing adenine. Also, in case of Example 20, the yield and purity of adenine are lowered because of a high water content of phenylazomalononitrile.

COMPARATIVE EXAMPLE 4

By employing the phenylazomalononitrile obtained in Example 16, adenine was prepared in the same manner as in Example 14(ii) except that ammonia was not removed.

The result is shown in Table 6.

COMPARATIVE EXAMPLE 5

By employing the phenylazomalononitrile obtained in Example 17, adenine was prepared in the same manner as in Example 14(ii) except that ammonia was not removed.

The result is shown in Table 6.

COMPARATIVE EXAMPLE 6

In 680 g. of formamide containing 6% by weight of ammonia was dissolved 68.1 g. of the phenylazomalononitrile obtained in Example 18, and the reaction was carried out in an autoclave at a temperature of 150° to 155° C. for 3 hours.

After cooling the reaction mixture to room temperature, 10 g. of Raney nickel was added thereto and the catalytic reduction was carried out at a temperature of 130° to 135° C. under an initial hydrogen pressure of 50 kg./cm.$^2$. After 1.5 hours, the absorption of hydrogen was 75% of theoretical. The temperature was then raised, and the reaction was further continued at a temperature of 150° to 155° C. for 4 hours. The reaction mixture was cooled and taken out from the autoclave, and excess formamide was recovered by reduced pressure distillation. To the residue was added 2.5 liters of water, and the mixture was refluxed to dissolve adenine. After removing insoluble materials by filtration, 20 g. of active carbon was added to the filtrate and decoloration was conducted by refluxing for hour. The hot solution was filtered to remove active carbon, and the filtrate was cooled to precipitate adenine. The crystal was filtered and dried. The result is shown in Table 6.

COMPARATIVE EXAMPLE 7

By employing the phenylazomalononitrile obtained in Example 19, adenine was prepared in the same manner as in Comparative Example 6.

The result is shown in Table 6.

COMPARATIVE EXAMPLE 8

By employing the phenylazomalononitrile obtained in Example 20, adenine was prepared in the same manner as in Example 14(ii) except that ammonia was not removed.

The result is shown in Table 6.

TABLE 6

| Com. Ex. No. | Adenine Amount (g.) | Yield (%) | Impurity (% by weight) |
|---|---|---|---|
| 4 | 30.7 | 56.8 | 5.31 |
| 5 | 28.3 | 52.4 | 5.77 |
| 6 | 22.9 | 42.4 | 3.19 |
| 7 | 25.4 | 47.0 | 4.50 |
| 8 | 23.3 | 43.1 | 6.02 |

EXAMPLE 21

In 680 g. of formamide containing 6% by weight of ammonia was dissolved 68.1 g. of phenylazomalononitrile, and the reaction was carried out in an autoclave at a temperature of 150° to 155° C. for 2 hours. Ammonia gas was then released from the still hot reaction mixture.

After cooling the reaction mixture, 10 g. of Raney nickel was added to the reaction mixture, and the catalytic reaction was carried out at a temperature of 150° to 155° C. for 5 hours under an initial hydrogen pressure of 80 kg./cm.$^2$. The reaction mixture was cooled and taken out from the autoclave, and formamide was recovered by reduced pressure distillation. The residue was then washed with methanol to give 44.2 g. of crude adenine.

To 500 ml. of purified water was added 10 g. of the crude adenine, and after heating and adjusting to pH 8.5 with a 48% by weight aqueous solution of sodium hydroxide at 80° to 90° C., the mixture was heated at 90° to 95° C. for 1 hour to dissolve adenine. The still hot solution was filtered to remove the catalyst and insoluble materials, and the filtrate was allowed to stand at 10° C. for 10 hours to precipitate adenine. The crystal was then filtered with suction and washed with a small amount of purified water. The obtained crystal was added to 100 ml. of purified water, and to the resulting suspension was gradually added a concentrated sulfuric acid to adjust to pH 2.0. The suspension was heated to dissolve the crystal, and after adding active carbon, was refluxed for 1 hour to decolor. The hot solution was filtered to remove active carbon, and the filtrate was cooled and the resulting crystal was filtered. The thus obtained sulfuric acid salt was dissolved in 500 ml. of purified water, and the solution was adjusted to pH 6.5 to 7 with sodium hydroxide. After adding a small amount of active carbon and heating the solution for 30 minutes, active carbon was filtered off and the filtrate was cooled to precipitate a white crystal of adenine. The crystal was filtered, washed sufficiently with purified water and dried to give 7.5 g. of adenine.

The purity of the thus purified adenine was 99.8% by weight and the content of impurity was 0.083% by weight. Also, the whiteness measured at 430 nm. was 95.2%.

EXAMPLE 22

The procedure of Example 21 was repeated except that in the purification of the crude adenine, hydrochloric acid was employed instead of sulfuric acid to give 6.9 g. of the purified adenine. The results are as follows:

Purity: 100.3% by weight
Impurity: 0.096% by weight
Whiteness: 95.0%

EXAMPLE 23

The procedure of Example 21 was repeated except that in the purification of the crude adenine, a 75% by weight phosphoric acid was employed instead of surfuric acid and the produced phosphoric acid salt was dissolved in 180 ml. of purified water, to give 7.8 g. of the purified adenine. The results are as follows:
Purity: 99.5% by weight
Impurity: 0.033% by weight
Whiteness: 96.1%

EXAMPLE 24

By employing 10 g. of the crude adenine obtained in Example 21, purification was carried out by adding the crude adenine to 500 ml. of water, refluxing to dissolve it, filtering the hot solution to remove insoluble materials, refluxing the filtrate for 1 hour with active carbon, and filtering off the active carbon. The filtrate was still tinged with pale brown, and thus the decoloration was repeated again by employing active carbon, and 7.8 g. of purified adenine was obtained from the filtrate. The results are as follows:
Purity: 98.1% by weight
Impurity: 0.42% by weight
Whiteness: 83.4%

The above results show that a conventional purification method is not so good in purity, content of impurity and whiteness as compared with the particular purification method according to the present invention.

EXAMPLES 25 TO 28

The procedures of Example 21 were repeated except that in the purification of the crude adenine, the removal of insoluble materials was conducted by using sodium hydroxide in combination with an inorganic salt shown in Table 7 at pH shown in Table 7 and the decoloration was conducted by employing an acid shown in Table 7 at pH shown in Table 7.

The results are shown in Table 7.

TABLE 7

| Ex. No. | Removal of insoluble materials | | | | | Adenine | | |
|---|---|---|---|---|---|---|---|---|
| | Inorganic salt | | | Decoloration | | Amount (g.) | Purity (% by weight) | impurity (% by weight) | Whiteness (%) |
| | Kind | Amount (g.) | pH | Acid | pH | | | | |
| 25 | Na2SO4 | 3 | 8.5 | H2SO4 | 1.8 | 7.8 | 99.6 | 0.04 | 95.2 |
| 26 | Na2SO4 | 4 | 8.3 | H3PO4 | 2.0 | 7.7 | 100.3 | 0.05 | 95.8 |
| 27 | NaCl | 3 | 8.0 | H2SO4 | 1.8 | 7.2 | 99.4 | 0.09 | 93.6 |
| 28 | NH4Cl | 3 | 8.0 | H2SO4 | 2.2 | 7.4 | 99.6 | 0.08 | 93.8 |

EXAMPLE 29

The procedure of Example 21 was repeated except that in the purification of the crude adenine, 5 ml. of hydrogen peroxide (30% by weight) was employed instead of sodium hydroxide used for pH adjustment, to give 7.1 g. of purified adenine. The results are as follows:
Purity: 98.0% by weight
Impurity: 1.5% by weight
Whiteness: 92.5%

The above results show that oxidation is not effective for the removal of impurities.

EXAMPLE 30

To 500 ml. of purified water were added 10.0 g. of the crude adenine obtained in Example 21 and 4.5 g. of Glauber's salt, and the mixture was heated to 80° to 90° C., adjusted to pH 8.0 with a 48% by weight aqueous solution of sodium hydroxide and heated to 90° to 95° C. to dissolve adenine. Insoluble materials was filtered off and the filtrate was adjusted to pH 2.5 with 30% by weight sulfuric acid. Active carbon was then added to the solution, and decoloration was conducted by heating for 1 hour. After filtering off the active carbon, the filtrate was neutralized to pH 7 with a 48% by weight aqueous solution of sodium hydroxide. A small amount of active carbon was added to the filtrate, and after conducting decoloration again and filtering off the active carbon, the filtrate was cooled to precipitate crystal of adenine. The crystal was filtered with suction, washed with purified water and dried to give 8.5 g. of adenine. The results are as follows:
Purity: 99.3% by weight
Impurity: 0.12% by weight
Whiteness: 93.6%

What we claim is:

1. In a continuous process for preparing adenine by reacting an arylazomalononitrile of the formula:

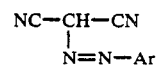

wherein Ar is an aryl group, with formic acid or its derivatives in the presence of ammonia at an elevated temperature to produce a 4,6-diamino-5-arylazopyrimidine and subjecting the resulting reaction mixture to a reaction under a catalytic reduction condition in which catalytic reduction of the 4,6-diamino-5-arylazopyrimidine and cyclization of the resulting 4,5,6-triaminopyrimidine into adenine takes place, the improvement which comprises removing ammonia from said resulting reaction mixture and carrying out the catalytic reduction in the substantial absence of ammonia, and wherein said arylazomalononitrile is prepared by coupling a diazonium salt with malononitrile at a temperature of not more than 25° C. at pH 3.5 to 5.5 and drying the resulting coupling reaction product to not more than 5% by weight in water content.

2. The process of claim 1, wherein said diazonium salt is one prepared by reacting an aromatic amine with sodium nitrite at a temperature of not more than 12° C.

3. In a continuous process for preparing adenine by reacting an arylazomalononitrile of the formula:

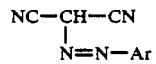

wherein Ar is an aryl group, with formic acid or its derivatives in the presence of ammonia at an elevated temperature to produce a 4,6-diamino-5-arylazopyrimidine and subjecting the resulting reaction mixture to a reaction under a catalytic reduction condition in which catalytic reduction of the 4,6-diamino-5-arylazopyrimidine and cyclization of the resulting 4,5,6-triaminopyrimidine into adenine take place, the improvement which comprises removing ammonia from said resulting reaction mixture and carrying out the catalytic reduction in the substantial absence of ammonia, and in the presence of a Raney nickel catalyst, and 1 to 300% by weight of active carbon based on the Raney nickel catalyst.

4. In a continuous process for preparing adenine by reacting an arylazomalononitrile of the formula:

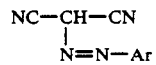

wherein Ar is an aryl group, with formic acid or its derivatives in the presence of ammonia at an elevated temperature to produce a 4,6-diamino-5-arylazopyrimidine and subjecting the resulting reaction mixture to a reaction under a catalytic reduction condition in which catalytic reduction of the 4,6-diamino-5-arylazopyrimidine and cyclization of the resulting 4,5,6-triaminopyrimidine into adenine take place, the improvement which comprises removing ammonia from said resulting reaction mixture and carrying out the catalytic reduction in the substantial absence of ammonia, recovering adenine from the reaction mixture in the reaction under a catalytic reduction condition, and purifying the adenine by dissolving it in hot water at pH 7.5 to 9.0, separating insoluble materials, adding a mineral acid to the solution of adenine to form a mineral acid salt of adenine and decolorizing the solution with activated carbon.

5. The process of claim 4, wherein said mineral acid is a member selected from the group consisting of sulfuric acid, phosphoric acid and hydrochloric acid.

6. The process of claim 4, wherein an inorganic salt selected from the group consisting of Glauber's salt, sodium chloride, ammonium chloride, ammonium carbonate and ammonium dihydrogenphosphate is present in the hot water adjusted to pH 7.5 to 9.0.

* * * * *